(12) United States Patent
Bailey et al.

(10) Patent No.: US 11,298,505 B2
(45) Date of Patent: Apr. 12, 2022

(54) DEPLOYABLE BELLOWS FOR DELIVERY OF A FLEXIBLE, ELONGATE DEVICE AND METHODS OF USE

(71) Applicant: INTUITIVE SURGICAL OPERATIONS, INC., Sunnyvale, CA (US)

(72) Inventors: David W. Bailey, Portota Valley, CA (US); Jared J. Butler, Provo, UT (US); Larry L. Howell, Orem, UT (US); Brian D. Jensen, Orem, UT (US); Spencer P. Magleby, Provo, UT (US); Brandon Scott Sargent, Provo, UT (US); Kendall Hal Seymour, Provo, UT (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 545 days.

(21) Appl. No.: 16/291,398

(22) Filed: Mar. 4, 2019

(65) Prior Publication Data

US 2019/0269885 A1    Sep. 5, 2019

Related U.S. Application Data

(60) Provisional application No. 62/638,718, filed on Mar. 5, 2018.

(51) Int. Cl.
*A61B 34/00* (2016.01)
*A61M 25/00* (2006.01)
(Continued)

(52) U.S. Cl.
CPC ... *A61M 25/0054* (2013.01); *A61B 17/00234* (2013.01); *A61B 34/20* (2016.02); *A61B 34/30* (2016.02); *A61B 34/74* (2016.02); *A61M 25/0029* (2013.01); *A61M 25/0053* (2013.01); *A61B 2017/003* (2013.01); *A61B 2034/2055* (2016.02); *A61B 2034/2065* (2016.02); *A61B 2034/301* (2016.02); *A61B 2034/741* (2016.02); *A61B 2034/742* (2016.02); *A61M 2025/0059* (2013.01)

(58) Field of Classification Search
CPC ........ A61B 2017/003; A61B 2034/301; A61B 2034/2059; A61M 2025/0059
See application file for complete search history.

(56) References Cited

U.S. PATENT DOCUMENTS

| 6,054,194 A  * | 4/2000 | Kane ...................... B60D 5/003 105/18 |
| 2004/0045561 A1 * | 3/2004 | Alexander ........... G09B 23/285 128/897 |

OTHER PUBLICATIONS

BRBF System, "BRBF Introduction, Concept of Buckling Restrained Brace, Pinned Brace, Powercat, Welded Brace, Wildcat," retreived on Sep. 19, 2018, Retrieved from the internet URL: http://www.starseismic.eu/BRBF_system, 6 pages.

(Continued)

*Primary Examiner* — Jason M Ip
(74) *Attorney, Agent, or Firm* — Haynes and Boone, LLP

(57) ABSTRACT

An origami bellows includes a plurality of layers including a support layer having a diameter that remains fixed irrespective of axial expansion or compression of the origami bellows. The origami bellows may be used as an anti-buckling device providing lateral support to a catheter or other elongated medical instrument.

20 Claims, 12 Drawing Sheets

(51) Int. Cl.
*A61B 17/00* (2006.01)
*A61B 34/20* (2016.01)
*A61B 34/30* (2016.01)

(56) References Cited

OTHER PUBLICATIONS

Butler J., et al., "Highly Compressible Origami Bellows for Harsh Environments," Proceedings of the ASME 2016 International Design Engineering Technical Conferences andComputers and Information in Engineering Conference (IDETC/CIE), DETC2016-59060, Aug. 2016, 11 pages.
Butler J., et al., "Highly Compressible Origami Bellows for Microgravity Drilling-Debris Containment," AIAA Space and Astronautics Forum and Exposition, 2017, 16 pages.
Jianguo C., et al., "Bistable Behavior of the Cylindrical Origami Structure With Kresling Pattern," Journal of Mechanical Design, Jun. 2015, vol. 137 (6), pp. 061406-1-061406-8.
Kresling B., Natural Twist Buckling in Shells: from the Hawkmoth's Bellow to the Deployable "Kresling-pattern" and Cylindrical "Miura-ori", Proceedings of the 6th International Conference on Computation of Shell and Spatial Structures, IASS-IACM 2008:"Spanning Nano to Mega", May 2008, 4 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

\* cited by examiner

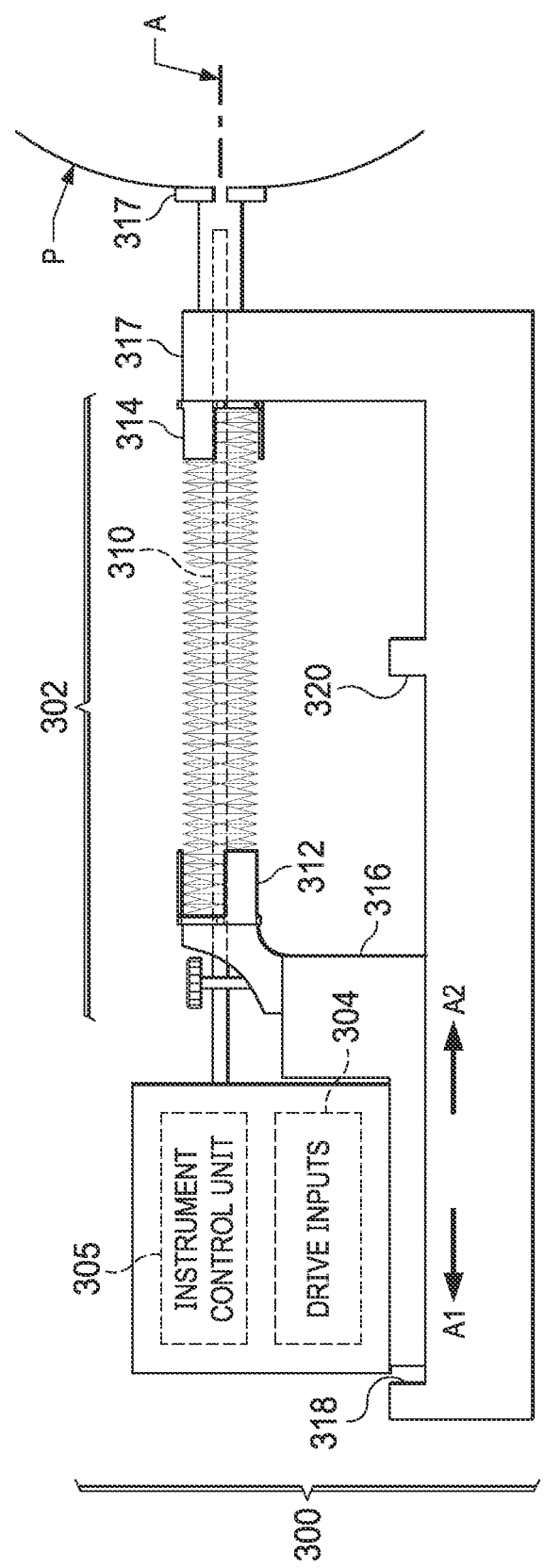

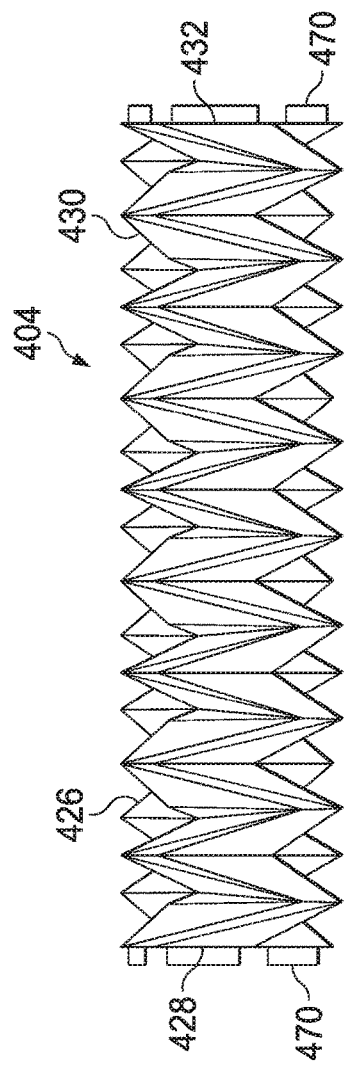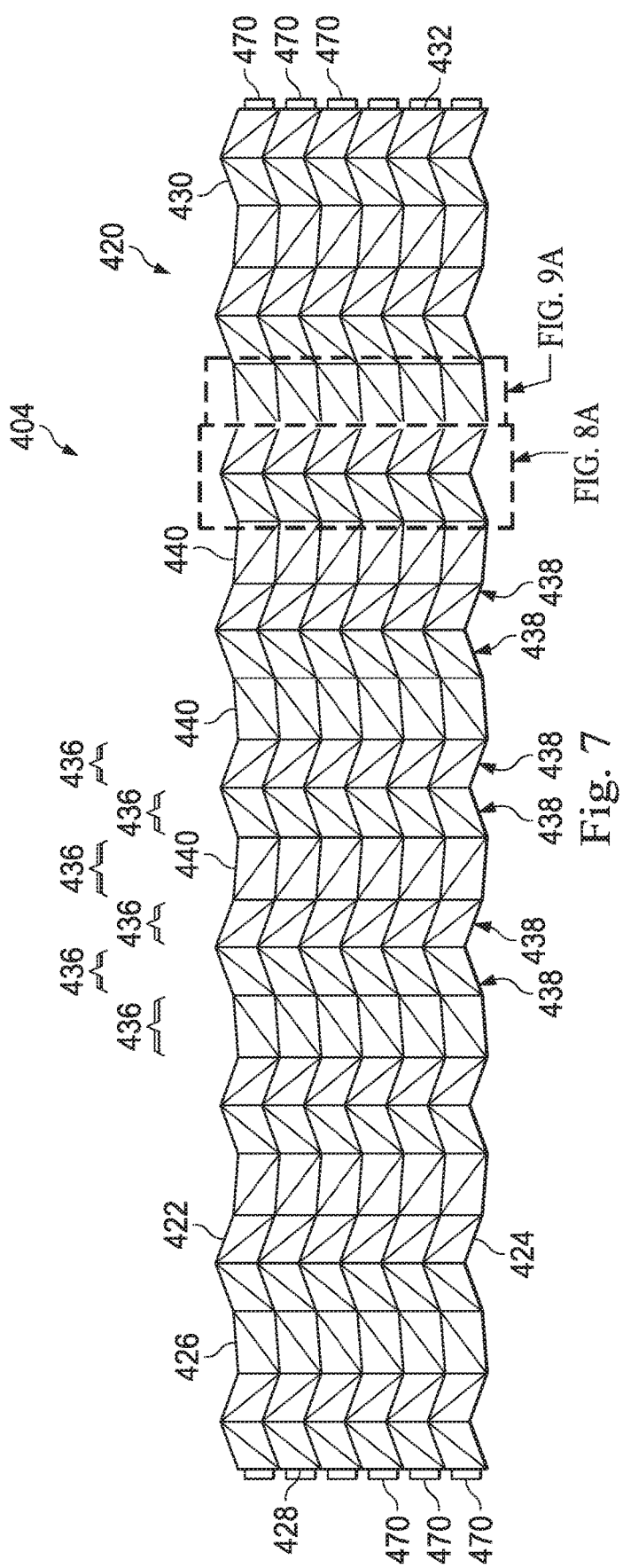

DEPLOYABLE BELLOWS FOR DELIVERY OF A FLEXIBLE, ELONGATE DEVICE AND METHODS OF USE

CROSS-REFERENCE TO RELATED APPLICATIONS

This application claims the benefit of U.S. Provisional Application 62/638,718 filed Mar. 5, 2018, which is incorporated by reference herein in its entirety.

FIELD

The present disclosure is directed to systems and methods for delivering and supporting an elongate device (such as a flexible interventional instrument and/or a steerable interventional instrument) into a patient anatomy.

BACKGROUND

Minimally invasive medical techniques are intended to reduce the amount of tissue that is damaged during interventional procedures, thereby reducing patient recovery time, discomfort, and harmful side effects. Such minimally invasive techniques may be performed through natural orifices in a patient anatomy or through one or more surgical incisions. Through these natural orifices or incisions clinicians may insert interventional instruments (including surgical, diagnostic, therapeutic, or biopsy instruments) to reach a target tissue location. Physicians may insert minimally invasive medical instruments (including surgical, diagnostic, therapeutic, or biopsy instruments) through these natural orifices or incisions to reach a target tissue location. One such minimally invasive technique is to use a flexible and/or steerable elongate device, such as a flexible catheter, that can be inserted into anatomic passageways and navigated toward a region of interest within the patient anatomy. To reach the target tissue location, a minimally invasive interventional instrument may navigate natural or surgically created passageways in anatomical systems such as the lungs, the colon, the intestines, the kidneys, the heart, the circulatory system, or the like. Control of such an elongate device by medical personnel involves the management of several degrees of freedom including at least the management of insertion and retraction of the elongate device as well as steering of the device. In addition, different modes of operation may also be supported.

Teleoperational interventional systems may be used to insert the flexible interventional instruments into the patient anatomy. Several interventional instruments are made of flexible material that allows for maneuverability through a patient's body. In existing systems, at least a portion of the interventional instrument extending between the patient and a manipulator is unsupported, and the flexible nature of the instrument can cause it to bend, twist, or buckle in an undesirable manner at a point external to the patient's body when force is exerted to insert the instrument into the patient's anatomy. Deformation of the instrument may damage internal components such as optical fiber shape sensors or endoscopic equipment. While current systems may provide adequate support for these types of instruments, additional improvements may be had for guiding and supporting interventional instruments as they are inserted into a patient anatomy to prevent instrument deformation.

SUMMARY

The implementations of the invention are summarized by the claims that follow the description. In some aspects, the present disclosure is directed to a catheter anti-buckling device used to provide lateral support to a catheter. As the catheter advances and retracts, the anti-buckling device longitudinally compresses and expands. In some aspects, the antibuckling device is a single-sheet origami device that axially compresses and expands. The catheter may be disposed in a lumen of the origami device, and the supporting lateral sides of the origami device may inhibit or prevent catheter buckling. In some aspects, an anti-buckling origami bellows has rigid layers that provide a fixed inner diameter even as the tube compresses and expands. The origami device described may be used in the implementation where a substantially fixed inner diameter is desired.

Consistent with some implementations, the present disclosure is directed to a deployable bellows apparatus for laterally supporting a flexible elongate device introducible using a manipulator assembly. The apparatus may include an origami bellows having a distal end, a proximal end, and a lumen extending from the distal end to the proximal end. The origami bellows may be axially compressible from an expanded condition to a compressed condition. A first connector may be disposed at and coupled to the distal end. The first connector may be configured to connect the distal end to the manipulator assembly. A second connector may be disposed at and coupled to the proximal end. The second connector may be configured to connect the proximal end to the manipulator assembly. In some aspects, the lumen may be sized to provide lateral support to the flexible elongate device as the flexible elongate device extends therethrough.

In another exemplary implementation, the present disclosure is directed to a method that may include introducing a flexible elongated instrument into a lumen of an origami bellows, the lumen having walls forming an inner diameter; and advancing the flexible elongated instrument while simultaneously compressing the origami bellows so that walls of the lumen laterally support the flexible elongated instrument and reduce a likelihood of buckling. In some aspects, the method may include introducing the flexible elongated instrument into a passage of a first connector aligned with the lumen of the origami bellows so that the flexible elongated instrument extends through the passage and into the lumen.

In another exemplary implementation, the present disclosure is directed to deployable origami bellows apparatus that includes a distal end, a proximal end, and a lumen extending from the distal end to the proximal end. The origami bellows may be axially actuatable between an expanded condition to a compressed condition, and may include a plurality of layers including at least one monostable layer that may be stable in one of a compressed or extended condition, and including at least one bistable layer adjacent the monostable layer that may be stable in the compressed condition and in the expanded condition.

In another exemplary implementation, the present disclosure is directed to an apparatus that includes an origami bellows formed of a single monolithic material and axially compressible from an extended condition to a compressed condition. The origami bellows may include a distal end, a proximal end, and a lumen extending from the distal end to the proximal end. The origami bellows may include a plurality of first layers having a first inner diameter forming a part of the lumen, wherein the first inner diameter changes when the origami bellows moves between an expanded condition and a compressed condition. The origami bellows also may include a plurality of wall portions having a second inner diameter forming a part of the lumen. The second inner diameter may be unchanged when the origami bellows moves between an extended condition and a compressed condition. In some aspects, each wall portion of the plurality of wall portions is formed of a second layer of the origami bellows, with each second layer having the unchanging second diameter.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various implementations and/or configurations discussed.

FIG. 3 is a simplified diagram of a side view of a manipulator assembly, an elongate instrument, and an instrument guiding apparatus according to some implementations of the present invention.

FIG. 6 is a diagram of a side view of an origami bellows forming a portion of the instrument guiding apparatus of FIG. 5 in a partially deployed condition according to some implementations of the present disclosure.

FIG. 7 is a diagram of a plan view of a sheet material for forming the origami bellows of FIG. 6 according to some implementations of the present disclosure.

Figure 1:
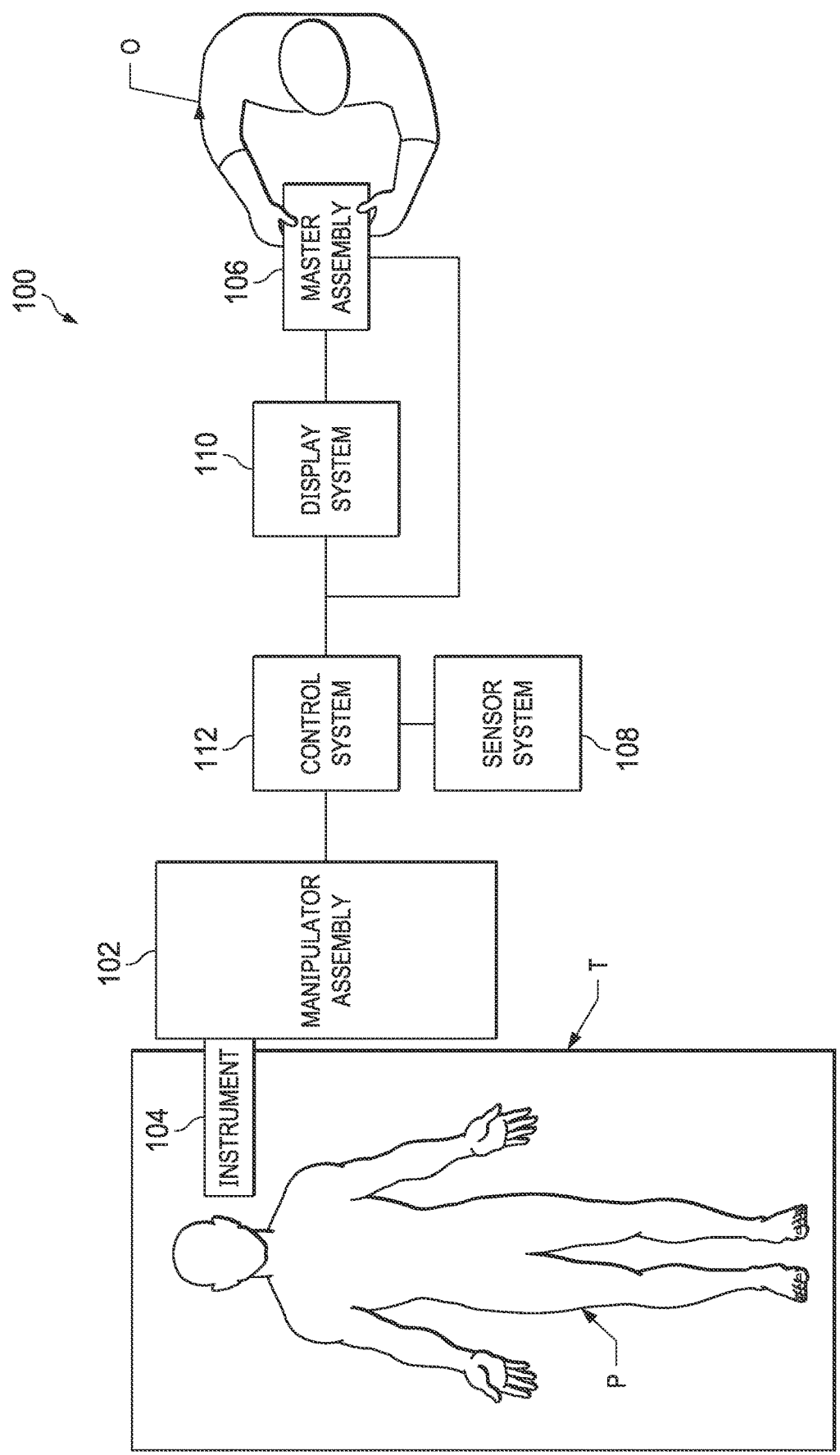
FIG. 1 is a simplified diagram of a teleoperated medical system according to some implementations of the present disclosure.

Implementations of the present disclosure and their advantages are best understood by referring to the detailed description that follows. It should be appreciated that like reference numerals are used to identify like elements illustrated in one or more of the figures, wherein showings therein are for purposes of illustrating implementations of the present disclosure and not for purposes of limiting the same.

DETAILED DESCRIPTION

In the following description, specific details are set forth describing some implementations consistent with the present disclosure. Numerous specific details are set forth in order to provide a thorough understanding of the implementations. It will be apparent, however, to one skilled in the art that some implementations may be practiced without some or all of these specific details. The specific implementations disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one implementation may be incorporated into other implementations unless specifically described otherwise or if the one or more features would make an implementation non-functional.

In some instances well known methods, procedures, components, and circuits have not been described in detail so as not to unnecessarily obscure aspects of the implementations.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

FIG. 1 is a simplified diagram of a teleoperated medical system 100 according to some implementations. In some implementations, teleoperated medical system 100 may be suitable for use in, for example, surgical, diagnostic, therapeutic, or biopsy procedures. As shown in FIG. 1, medical system 100 generally includes a manipulator assembly 102 for operating a medical instrument of the medical instrument system 104 in performing various procedures on a patient P. Manipulator assembly 102 is mounted to or near an operating table T. An operator input system 106 (sometimes called a master assembly 106) allows an operator O (e.g., a surgeon, a clinician, or a physician as illustrated in FIG. 1) to view the interventional site and to control manipulator assembly 102 or sub-assemblies within manipulator assembly 102.

Master assembly 106 may be located at an operator's console which is usually located in the same room as operating table T, such as at the side of a surgical table on which patient P is located. However, it should be understood that operator O can be located in a different room or a completely different building from patient P. Master assembly 106 generally includes one or more control devices for controlling manipulator assembly 102 or sub-assemblies within manipulator assembly 102. The control devices may include any number of a variety of input devices, such as joysticks, trackballs, data gloves, trigger-guns, hand-operated controllers, voice recognition devices, body motion or presence sensors, and/or the like. To provide physician O a strong sense of directly controlling instruments the control devices may be provided with the same degrees of freedom as the associated medical instrument of the medical instrument system 104. In this manner, the control devices provide physician O with telepresence or the perception that the control devices are integral with the medical instrument system 104.

In some implementations, the control devices may have more or fewer degrees of freedom than the associated medical instrument of the medical instrument system 104 and still provide physician O with telepresence. In some implementations, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

The manipulator assembly 102 supports the medical instrument system 104 and may include a kinematic structure of one or more non-servo controlled links (e.g., one or more links that may be manually positioned and locked in place, generally referred to as a set-up structure), a teleoperational structure, and/or a teleoperational manipulator. The manipulator assembly 102 includes plurality of actuators or motors that drive inputs on the medical instrument system 104 in response to commands from the control system (e.g., a control system 112). The motors include drive systems that when coupled to the medical instrument system 104 may advance the medical instrument into a naturally or surgically created anatomic orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like. Motor position sensors such as resolvers, encoders, potentiometers, and other mechanisms may provide sensor data to the manipulator assembly describing the rotation and orientation of the motor shafts. This position sensor data may be used to determine motion of the objects manipulated by the motors.

The teleoperational medical system 100 also includes a sensor system 108 with one or more sub-systems for receiving information about the instruments of the manipulator assembly. Such sub-systems may include a position/location sensor system (e.g., an electromagnetic (EM) sensor system); a shape sensor system for determining the position, orientation, speed, velocity, pose, and/or shape of the catheter tip and/or of one or more segments along a flexible body of instrument system 104; and/or a visualization system for capturing images from the distal end of the catheter system.

The visualization system (e.g., visualization system 231 of FIG. 2A) may include a viewing scope assembly that records a concurrent or real-time image of the surgical site and provides the image to the clinician or surgeon S. The concurrent image may be, for example, a two or three dimensional image captured by an endoscope positioned within the surgical site. In this implementation, the visualization system includes endoscopic components that may be integrally or removably coupled to the medical instrument system 104. However in alternative implementations, a separate endoscope, attached to a separate manipulator assembly may be used with the medical instrument to image the surgical site. The visualization system may be implemented as hardware, firmware, software or a combination thereof which interact with or are otherwise executed by one or more computer processors, which may include the processors of a control system 112 (described below). The processors of the control system 112 may execute instructions comprising instruction corresponding to processes disclosed herein.

The teleoperational medical system 100 also includes a display system 110 for displaying an image or representation of the surgical site and medical instrument system(s) 104 generated by sub-systems of the sensor system 108. The display system 110 and the master assembly 106 may be oriented so the physician O can control the medical instrument system 104 and the master assembly 106 with the perception of telepresence.

The display system 110 may also display an image of the surgical site and medical instruments captured by the visualization system. The display system 110 and the control devices may be oriented such that the relative positions of the imaging device in the scope assembly and the medical instruments are similar to the relative positions of the surgeon's eyes and hands so the operator can manipulate the medical instrument of the medical instrument system 104 and the hand control as if viewing the workspace in substantially true presence. By true presence, it is meant that the presentation of an image is a true perspective image simulating the viewpoint of an operator that is physically manipulating the instrument of the medical instrument system 104.

Alternatively or additionally, the display system 110 may present images of the surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The pre-operative or intra-operative image data may be presented as two-dimensional, three-dimensional, or four-dimensional (including e.g., time based or velocity based information) images or as images from models created from the pre-operative or intra-operative image data sets.

In some implementations, often for purposes of imaged guided surgical procedures, the display system 110 may display a virtual navigational image in which the actual location of the medical instrument of the medical instrument system 104 is registered (i.e., dynamically referenced) with the preoperative or concurrent images/model to present the physician O with a virtual image of the internal surgical site from the viewpoint of the location of the tip of the instrument of the medical instrument system 104. In some examples, the viewpoint may be from a tip of medical instrument of the medical instrument system 104. An image of the tip of the instrument of the medical instrument system 104 or other graphical or alphanumeric indicators may be superimposed on the virtual image to assist the physician O controlling the medical instrument. Alternatively, the instrument of the medical instrument system 104 may not be visible in the virtual image.

In other implementations, the display system 110 may display a virtual navigational image in which the actual location of the medical instrument is registered with preoperative or concurrent images to present the physician O with a virtual image of medical instrument within the surgical site from an external viewpoint. An image of a portion of the medical instrument or other graphical or alphanumeric indicators may be superimposed on the virtual image to assist the physician O controlling the instrument of the medical instrument system 104. As described herein, visual representations of data points may be rendered to the display system 110. For example, measured data points, moved data points, registered data points, and other data points described herein may be displayed on the display system 110 in a visual representation. The data points may be visually represented in a user interface by a plurality of points or dots on the display or as a rendered model, such as a mesh or wire model created based on the set of data points. In some implementations, a visual representation may be refreshed in the display system 110 after each processing operations has been implemented to alter the data points.

The teleoperational medical system 100 also includes a control system 112. The control system 112 includes at least one memory and at least one computer processor (not shown), and typically a plurality of processors, for effecting control between the medical instrument system 104, the master assembly 106, the sensor system 108, and the display system 110. The control system 112 also includes programmed instructions (e.g., a non-transitory machine-readable medium storing the instructions) to implement some or all of the methods described in accordance with aspects disclosed herein, including instructions for providing pathological information to the display system 110. While control system 112 is shown as a single block in the simplified schematic of FIG. 1, the system may include two or more data processing circuits with one portion of the processing optionally being performed on or adjacent the teleoperational assembly 102, another portion of the processing being performed at the master assembly 106, another portion of the processing being performed at master assembly 106, and the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one implementation, control system 112 supports wireless communication protocols such as Bluetooth, IrDA, HomeRF, IEEE 802.11, DECT, and Wireless Telemetry.

In some implementations, control system 112 may receive force and/or torque feedback from medical instrument of the medical instrument system 104. Responsive to the feedback, control system 112 may transmit signals to master assembly 106. In some examples, control system 112 may transmit signals instructing one or more actuators of manipulator assembly 102 to move medical instrument of the medical instrument system 104. Medical instrument of the medical instrument system 104 may extend into an internal surgical site within the body of patient P via openings in the body of patient P. Any suitable conventional and/or specialized actuators may be used. In some examples, the one or more actuators may be separate from, or integrated with, manipulator assembly 102. In some implementations, the one or more actuators and manipulator assembly 102 are provided as part of a teleoperational cart positioned adjacent to patient P and operating table T.

The control system 112 may further include a virtual visualization system to provide navigation assistance to physician O when controlling the medical instrument system(s) 104 during an image-guided surgical procedure. Virtual navigation using the virtual visualization system is based upon reference to the acquired preoperative or intra-operative dataset of the anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some implementations, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system.

The teleoperational medical system 100 may further include optional operation and support systems (not shown) such as illumination systems, steering control systems, irrigation systems, and/or suction systems. In some implementations, the teleoperational system may include more than one teleoperational assembly and/or more than one master assembly. The exact number of manipulator assemblies will depend on the surgical procedure and the space constraints within the operating room, among other factors. Master assembly 106 may be collocated or they may be positioned in separate locations. Multiple master assemblies allow more than one operator to control one or more manipulator assemblies in various combinations.

Figures 2A, 2B:
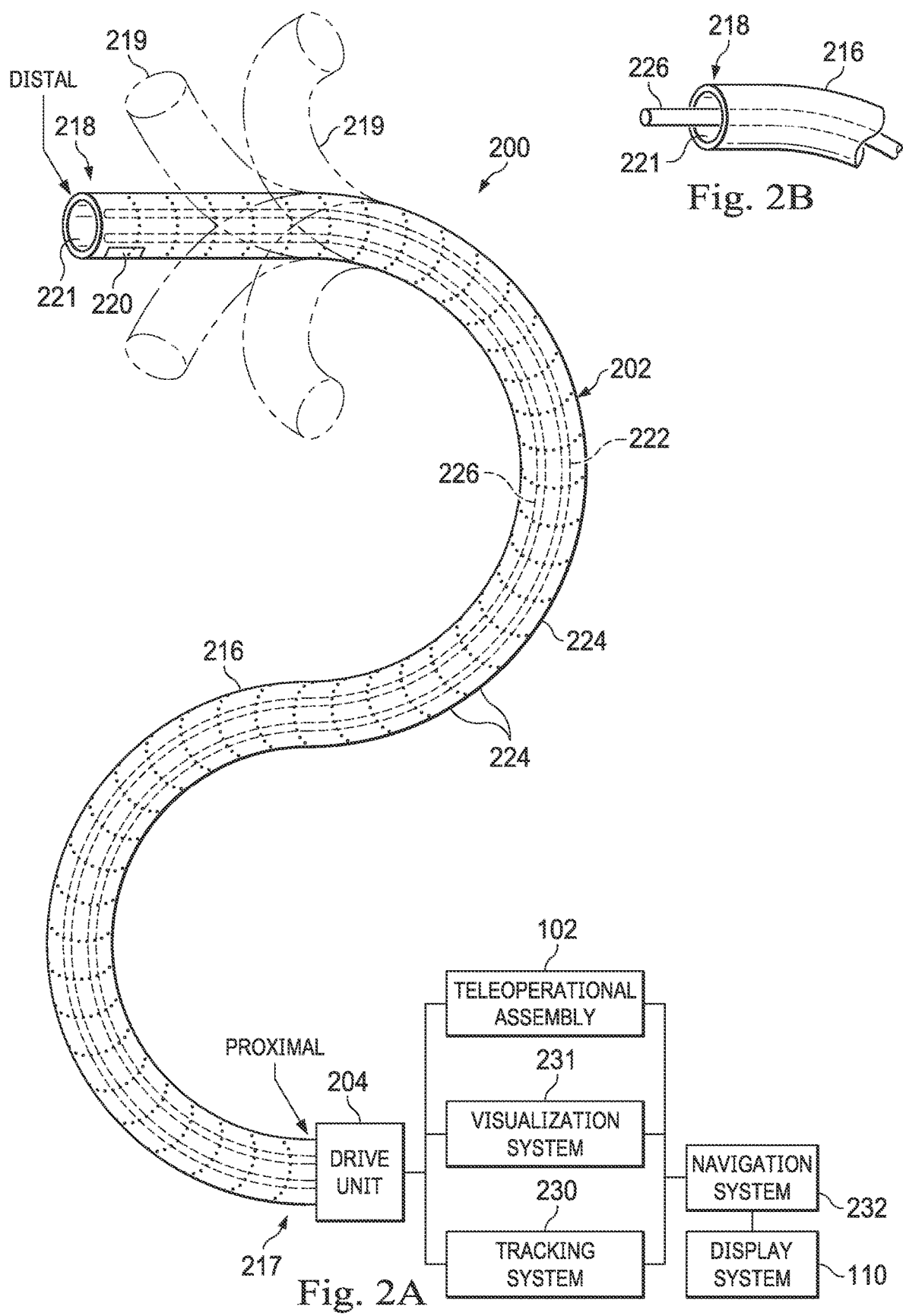
FIG. 2A is a simplified diagram of a medical instrument system according to some implementations of the present disclosure.
FIG. 2B is a simplified diagram of a medical instrument with an extended medical tool according to some implementations of the present disclosure.

FIG. 2A is a simplified diagram of a medical instrument system 200 according to some implementations. In some implementations, medical instrument system 200 may be used as medical instrument of the medical instrument system 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally, medical instrument system 200 may be used to gather (i.e., measure) a set of data points corresponding to locations within anatomic passageways of a patient, such as patient P.

The instrument system 200 includes a flexible, elongate device 202 (e.g., a catheter system) coupled to a drive unit 204. The elongate device 202 includes an elongated flexible body 216 having a proximal end 217 and a distal end 218 (or tip portion 218). In one implementation, the flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of distal end 218 and/or of one or more segments 224 along flexible body 216 using one or more sensors and/or imaging devices as described in further detail below. The entire length of flexible body 216, between distal end 218 and proximal end 217, may be effectively divided into segments 224. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one implementation, the optical fiber has a diameter of approximately 200 µm. In other implementations, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fiber Bend Sensor"), which are all incorporated by reference herein in their entireties. Sensors in some implementations may employ other suitable strain sensing techniques, such as Rayleigh scattering, Raman scattering, Brillouin scattering, and Fluorescence scattering. In some implementations, the shape of the elongate device may be determined using other techniques. For example, a history of the distal end pose of flexible body 216 can be used to reconstruct the shape of flexible body 216 over the interval of time. In some implementations, tracking system 230 may optionally and/or additionally track distal end 218 using a position sensor system 220. Position sensor system 220 may use any appropriate sensing technology or combination of sensing technologies, such as: OFDR (optical frequency domain reflectometry) techniques such as those using Fiber Bragg gratings, Raleigh scattering, or some other applicable reflection approach; position sensors enabled by EM (electromagnetic) techniques; linear rotary encoder techniques supported by capacitive, optical, resistive, or other technologies; etc. As a specific example, position sensor system 220 may comprise of, or be a component of, an EM sensor system with positional sensor system 220 including one or more conductive coils that may be subjected to an externally generated electromagnetic field. Each coil of such an EM sensor system used to implement position sensor system 220 then produces an induced electrical signal having characteristics that depend on the position and orientation of the coil relative to the externally generated electromagnetic field. In some implementations, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some implementations, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors used in some implementations of position sensor system 220 may be positioned along flexible body 216 and then used for shape sensing. In some examples, a history of data from one or more of these sensors taken during a procedure may be used to represent the shape of elongate device 202, particularly if an anatomic passageway is generally static.

Flexible body 216 includes a channel 221 sized and shaped to receive a medical instrument 226. FIG. 2B is a simplified diagram of flexible body 216 with medical instrument 226 extended according to some implementations. In some implementations, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various implementations, medical instrument 226 is a biopsy instrument, which may be used to remove sample tissue or a sampling of cells from a target anatomic location. Medical instrument 226 may be used with an image capture probe also within flexible body 216. In various implementations, medical instrument 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224. The image capture probe may include a cable coupled to the camera for transmitting the captured image data. In some examples, the image capture instrument may be a fiber-optic bundle, such as a fiberscope, that couples to visualization system 231. The image capture instrument may be single or multi-spectral, for example capturing image data in one or more of the visible, infrared, and/or ultraviolet spectrums. Alternatively, medical instrument 226 may itself be the image capture probe. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instrument 226 may additionally house cables, linkages, or other actuation controls (not shown) that extend between its proximal and distal ends to controllably the bend distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 218. Steerable elongate devices are described in detail in U.S. patent application Ser. No. 13/274,208 (filed Oct. 14, 2011) (disclosing "Catheter with Removable Vision Probe"), which is incorporated by reference herein in its entirety. In implementations in which medical instrument system 200 is actuated by a teleoperational assembly, drive unit 204 may include drive inputs that removably couple to and receive power from drive elements, such as actuators, of the teleoperational assembly. In some implementations, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some implementations, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the physician or other operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some implementations, manipulator assembly 102 of FIG. 1 may be replaced by direct operator control. In some examples, the direct operator control may include various handles and operator interfaces for hand-held operation of the instrument.

When using a teleoperational assembly to insert a catheter (or other flexible, elongate device or medical instrument) into a patient anatomy, the catheter length external to the patient should be supported as it is advanced into the patient. Otherwise, as the catheter is pushed from a proximal end and encounters friction in the patient anatomy at the distal end, the catheter may buckle or bend. To inhibit this deformation of the catheter, an instrument guiding apparatus may be used to provide support to the catheter either continuously along the catheter length or at regular intervals as it enters the patient anatomy along an insertion axis. In some implementations, the instrument guiding apparatus may include a deployable bellows or tube through which the catheter may extend. In some implementations, the deployable bellows may be maintained in tension to provide a sufficient level of stability and rigidity to the bellows to support the catheter. Generally, the catheter is introduced into the guiding apparatus while the apparatus is in a compressed condition. After a distal portion of the catheter is disposed through a distal portion of the guiding apparatus, the guiding apparatus can be expanded or deployed about the remainder of the catheter. The instrument guiding apparatus returns to an un-deployed condition as the catheter is advanced into the patient anatomy and the exposed length of the catheter decreases. As the catheter enters the patient anatomy, the guiding apparatus may compress. In some implementations, the instrument guiding apparatus described herein effectively provide stable support to the catheter as it is introduced into, traverses through, and is removed from the patient anatomy.

FIG. 3 diagrammatically illustrates an instrument interface portion 300 of a manipulator assembly (e.g., manipulator assembly 102) and an instrument guiding apparatus 302 according to an implementation of the present invention. The instrument interface portion 300 includes drive inputs 304 that may provide mechanical coupling of the instrument end effector and flexible body steering mechanism to the drive motors mounted to the manipulator. For example, a pair of drive inputs 304 may control the pitch motion of the distal end of the elongate flexible body (216 in FIG. 2A), with one adaptor of the pair controlling motion in the upward direction and the other of the pair controlling motion in the opposite downward direction. Other pairs of drive inputs 304 may provide opposing motion in other degrees of freedom for the flexible body and/or the end effector. In some implementations, the drive inputs 304 may be coupled to or positioned within an instrument control unit 305, which controls the positioning of an elongate instrument such as a catheter 310. Instrument interfacing with teleoperational or robotic manipulators is described, for example in U.S. Pat. No. 6,331,181, filed Oct. 15, 1999, disclosing "Surgical Robotic Tools, Data Architecture, And Use" and U.S. Pat. No. 6,491,701, filed Jan. 12, 2001 disclosing "Mechanical Actuator Interface System For Robotic Surgical Tools" which are both incorporated by reference herein in their entirety. The instrument interface portion 300 may also control instrument insertion by moving linearly along an insertion axis A.

During use, the catheter 310 is positioned within the instrument guiding apparatus 302 and the instrument guiding apparatus 302 acts to minimize the buckling of the catheter 310 as the catheter 310 advances toward, remains within, and retracts from the patient anatomy. The instrument guiding apparatus 302 has a proximal end 312 and a distal end 314. In some implementations, the proximal end 312 of the instrument guiding apparatus 302 is detachably coupled to a mounting plate 316 of the instrument interface portion 300. The mounting plate 316 may be moveable (e.g., along the insertion axis A) relative to a proximal end 318 and a distal end 320 of the instrument interface portion 300. The proximal end 318 and the distal end 320 may or may not be disposed at the physical ends of the instrument interface portion 300. For example, in the pictured implementation, the proximal end 318 and the distal end 320 comprise motion stops disposed away from the actual ends of the instrument interface portion 300 that are shaped and configured to halt the axial translation of the mounting plate 316. During use, the distal end 314 of the instrument guiding apparatus 302 may be detachably coupled to an anchor 317 within the surgical field. The anchor 317 may be positioned on the instrument interface portion 300 (e.g., on a flexible instrument manipulator or FIM), the surgical table, on a surgical frame, or on the patient anatomy. In one example, the anchor 317 may comprise a mouth guard clamped by patient's teeth. The instrument guiding apparatus 302 provides longitudinal support along the length of the catheter 310 positioned within the instrument guiding apparatus 302 to minimize buckling of the exposed length of the catheter 310 as it is pushed into the patient's body P.

Figure 4:
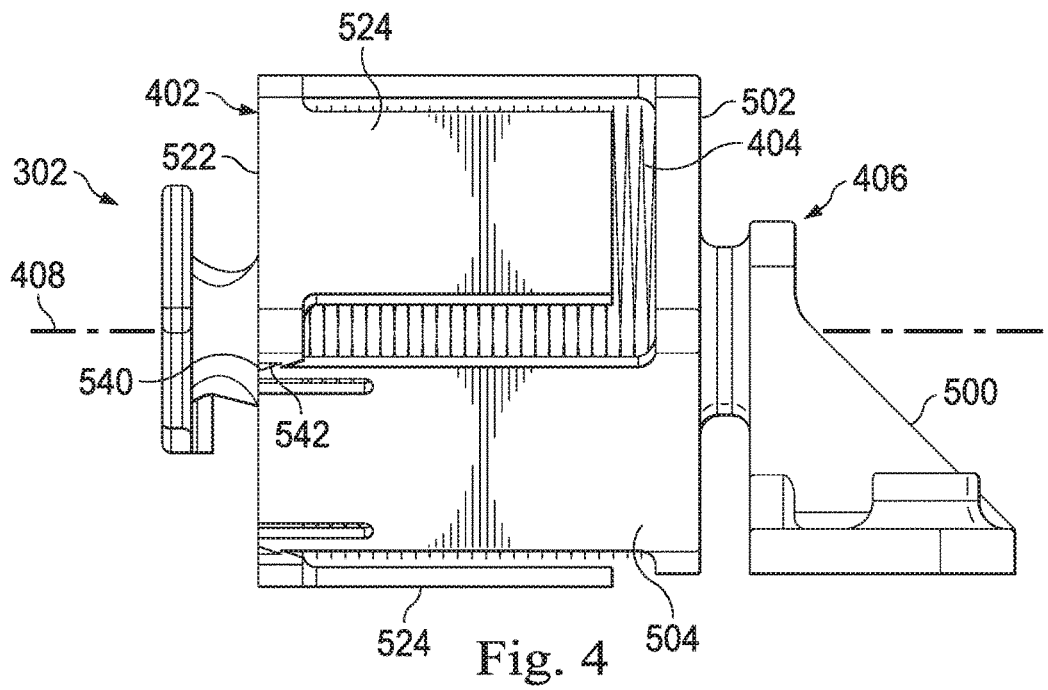
FIG. 4 is a diagram of a side view of an instrument guiding apparatus in a collapsed condition according to some implementations of the present disclosure.
Figure 5:
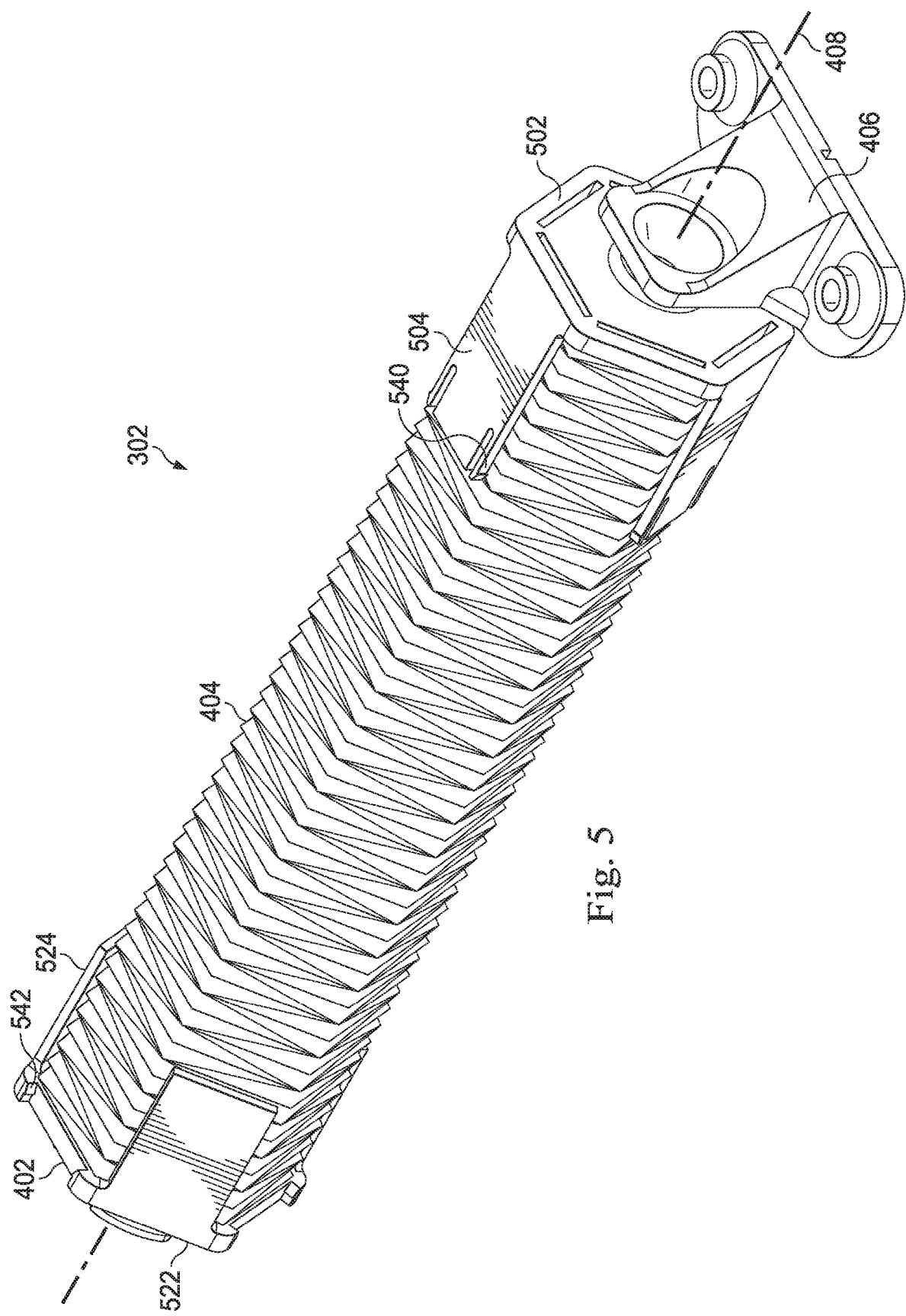
FIG. 5 is a diagram of a perspective view of a portion of the instrument guiding apparatus in a deployed condition according to some implementations of the present disclosure.

FIGS. 4-15 illustrate various views of the exemplary instrument guiding apparatus 302 according to some implementations of the present disclosure. In particular, FIG. 4 illustrates a side view of the instrument guiding apparatus 302 in a collapsed or compressed condition, and FIG. 5 illustrates a perspective view of the instrument guiding apparatus 302 in a deployed or expanded condition. The instrument guiding apparatus 302 includes a distal mount 402, an origami bellows 404, and a proximal mount 406. The distal mount 402 and the proximal mount 406 are each shaped and configured to attach to opposing ends of the origami bellows 404. The origami bellows 404 axially expands between a deployed condition and a compressed condition. That is, as the distal mount 402 and the proximal mount 406 translate toward or away from each other along the instrument interface portion 300, the origami bellows 404 axially expands and retracts along a longitudinally extending origami axis 408 between the compressed condition and the deployed condition. The catheter 310 (FIG. 3) extends coaxially with the origami axis 408, and the origami bellows provides lateral support to the catheter to constrain buckling or bending as the catheter is advanced toward or into a patient or in some instances, away from the patient.

FIGS. 6, 7, 8A, 8B, and 9A-9D show additional details of the origami bellows 404. The origami bellows 404 may be formed of a single, monolithic sheet material folded in a particular manner to allow consistent, repeatable deployment and compression of the origami bellows while substantially maintaining alignment about the origami axis 408. The sheet material forming the origami bellows 404 may be folded into a generally cylindrical shape, thereby forming an inner lumen having an inner diameter. To compress the origami bellows 404, the sheet material buckles under axial loading to form the collapsed or compressed condition. Some implementations of the origami bellows 404 include a plurality of distinct layers or stories formed from folds or bends in the single material sheet that distinctly perform particular functions. These different layers, built one upon the other, perform desired functions of supporting the catheter 310 and axially expanding and retracting, to increase or decrease the length of the origami bellows 404.

In some implementations, the distinct layers are formed of a geometric design comprising a plurality of triangular panels with cyclic symmetry. The geometry parameters such as size, length ratios of edges of the triangular panels, and the number of triangular panels together may determine the performance parameters of any particular layer. Depending on the geometric parameters, each layer of the origami bellows 404 may be either a bistable layer or a monostable layer. Bistable layers are selectively biased between different states independently of its neighboring adjacent layers, and therefore may switch between a collapsed condition and a deployed condition, depending on the amount of deployment. Monostable layers provide stability in conditions that are completely collapsed and are biased toward the collapsed state. Accordingly, the monostable layers lack intermediate stable condition. Bistable layers include intermediate stable conditions. In some implementations of the origami bellows 404 described herein, the origami bellows 404 includes both bistable and monostable layers.

Although described as being formed from a single sheet, in some implementations, the single sheet is made of a plurality of sheets independently cut out and then adhered together to form the cylinder with the proper folds or bends. In other implementations, the origami bellows is formed using a blow molding process.

Because some embodiments of the origami bellows 404 include different types of layers, each type of layer may form a differently sized inner diameter when in the collapsed condition. In some implementations, the origami bellows includes expansion layers (or actuation layers) and support layers. The expansion layers may be layers that axially expand the origami bellows 404. The support layers may be layers that laterally support the catheter 310. In some implementations described herein, the expansion layers may have an inner diameter that increases and decreases as the axial length of the origami bellows decreases and increases, while the support layers may have a substantially constant inner diameter that is maintained and fixed to provide lateral support to the catheter 310. Accordingly, the origami bellows 404 may remain monolithic while incorporating areas with fixed dinner diameters for support of the catheter. As indicated above, the multi-layered design may be made by repeating a number of different layers. Monostable layers provide for the actuation or axial expansion of the origami bellows. All the layers also rotate during actuation. In some implementations, these layers may be mirrored in order to cancel the overall rotation of the model during actuation. However, in some implementations, the layers are not in mirrored pairs and rotation may be permitted.

Bistable layers, which have a stable position in a compressed condition and in an expanded condition, may be used to support an internal member, such as the catheter 310. For example, the bistable layer may remain in the compressed condition, which means less actuation would occur in that layer and the inner diameter would be substantially constant or would change only minimally. In some implementations, an adhesive may be applied externally or internally to the bistable layer (or if desired, to a monostable layer) to adhere it or maintain it in the compressed condition. Once collapsed, the support layers have an unchanging inner diameter that supports the catheter. The support layer may be designed to have any desired internal diameter and therefore may accommodate any desired catheter size. In some implementations, the bellows may be designed such that support layers are stable in a closed configuration without being bonded. In such implementations, the inner diameter may be maintained at a laterally-supportive diameter, even as it fluctuates slightly in size.

In implementations where the bistable support layers remain unadhered, and therefore at least partially deploy and collapse during actuation, an even number of such layers (2, 4, 6, . . . ) may be used to cancel overall rotation in the origami bellows. Likewise, an even number of mirrored pairs of monostable layers may also cancel overall rotation. With such an arrangement, the ends of the origami bellows do not rotate relative to each other during actuation.

It is worth nothing that some implementations of the origami bellows include support layers that support the catheter axially. For example, the catheter may be press fit or otherwise connected to the support layer and support layer may axially advance or retract with the catheter affixed thereto as the origami bellows compresses and retracts.

FIG. 6 is a side view of the origami bellows 404 in an assembled or finished condition. FIG. 7 shows the sheet of material of the origami bellows 404 prior to being folded, and is referenced herein as sheet 420. In FIG. 7, the lines indicate the location of bends or folds in the material that will generate the layers, whether monostable or bistable, in the origami bellows 404. The sheet 420 includes nonlinear lateral edges 422 and 424. The origami bellows 404 may be created by rolling the sheet 420 and connecting the lateral edges 422 and 424 to form an approximately cylindrical bellows. Each of the origami bellows 404 and the sheet 420 includes a distal region 426 with a distal end 428 and a proximal region 430 with the proximal end 432. The sheet 420 includes a plurality of individual layers, referenced generally herein by the numeral 436. Of these layers 436, some are monostable layers referenced herein by the number 438, and some are bistable layers referenced herein by the number 440. The individual layers are made up of any number of parallelograms.

Figure 8A:
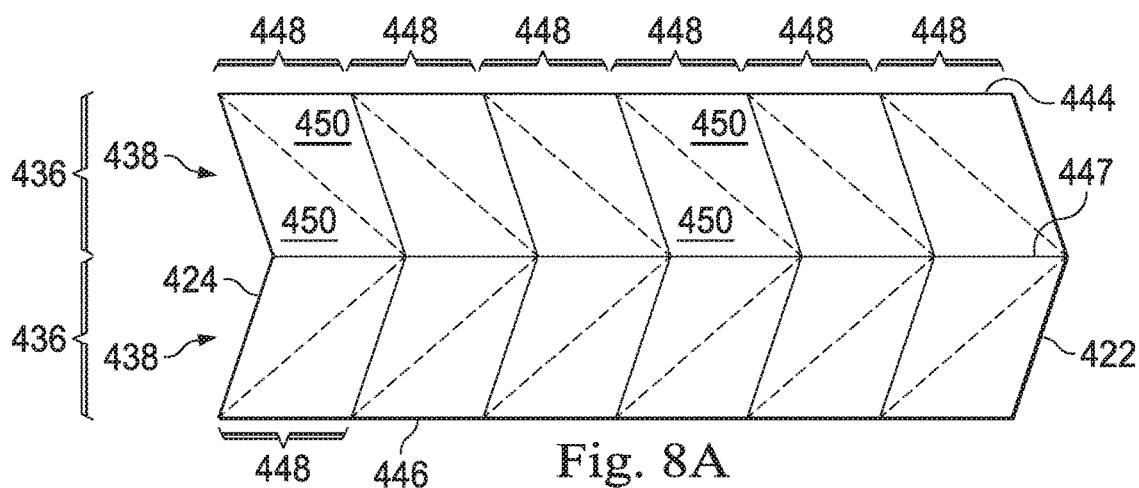
FIG. 8A is a diagram of a portion of the sheet material of FIG. 7 according to some implementations of the present disclosure.
Figure 8B:
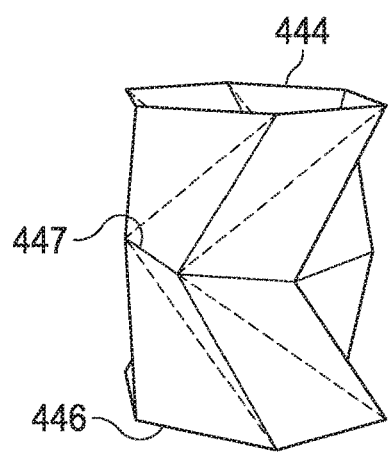
FIG. 8B is a diagram of a perspective view of an origami bellows formed of the portion of the sheet material shown in FIG. 8A according to some implementations of the present disclosure.

FIG. 8A shows additional detail of two of the monostable layers 438. Any particular layer 436 of the origami bellows 404 is formed of a combination of mountain folds and valley folds. In FIG. 8A, mountain folds are identified by solid lines, while valley folds are identified by dashed lines. The portion of the sheet shown in FIG. 8A includes an upper edge 444 and a lower edge 446. In this implementation, the portion of the sheet also includes six parallelogram panels 448 formed by mountain folds, with each parallelogram divided into two triangular panels 450 by the valley fold. In this example, the upper monostable layer 438 is a mirror image of the lower monostable layer. When rolled or otherwise made into a bellows, and folded with the mountain folds and valley folds identified, the portion of the sheet shown in FIG. 8A creates an origami bellows shown in FIG. 8B. This bellows is made by rolling the layers and attaching the lateral edges 422 and 424 to each other. Although each layer rotates as it collapses and expands, because the two layers in FIGS. 8A and 8B are mirror images, the edges 444, 446 may axially contract or expand without rotation. Naturally, the centerline 447 separating the layers will rotate as the bellows expands and retracts. Accordingly, the two layers in FIGS. 8A and 8B are actuation layers that axially expand and retract. As the two layers expand and retract, the inner diameter also expands and retracts.

Figure 9A:
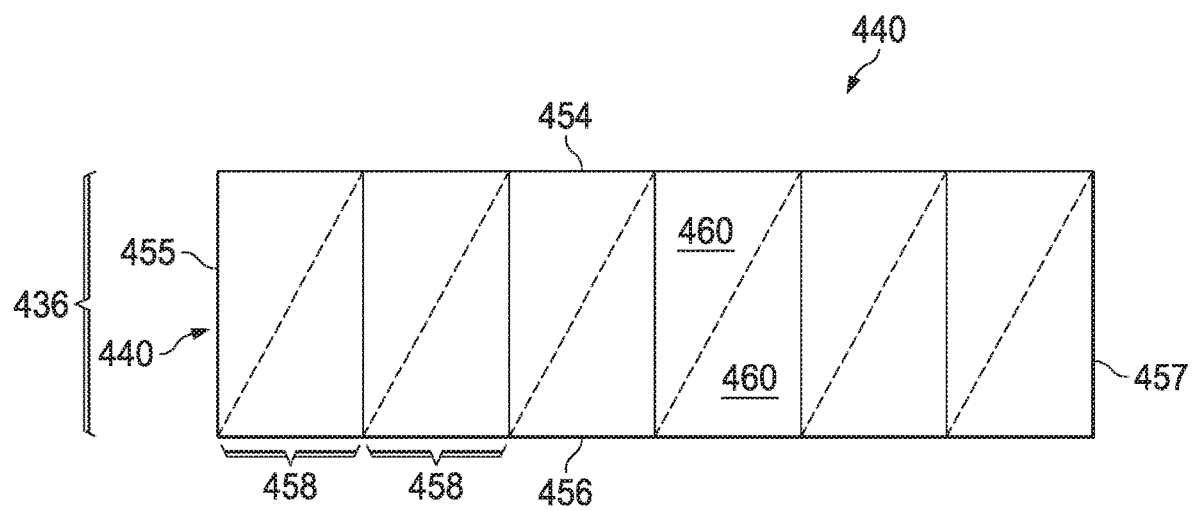
FIG. 9A is a detailed diagram of a portion of the sheet material of FIG. 7 according to some implementations of the present disclosure.
Figure 9B:
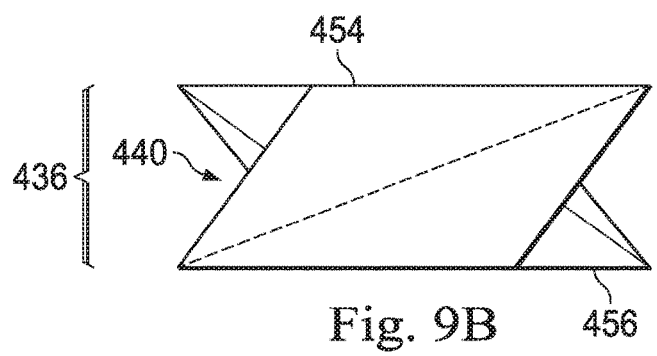
FIG. 9B is a diagram of a perspective view of an origami bellows formed of the portion of the sheet material shown in FIG. 9A according to some implementations of the present disclosure.
Figure 9C:
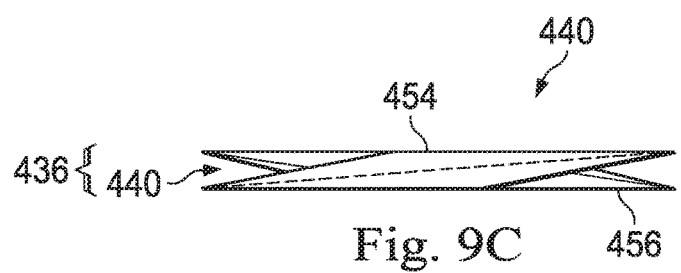
FIG. 9C is a side view diagram of an origami bellows formed of the portion of the sheet material shown in FIG. 9A according to some implementations of the present disclosure.

FIG. 9A shows additional detail of one of the bistable layers 440. As in FIG. 8A, solid lines represent mountain folds and dashed lines represent valley folds. The bistable layer 440 includes an upper edge 454 and a lower edge 456 and lateral edges 455 and 457. The bistable layer 440 in this example also includes six parallelogram panels 458 defined by mountain folds, with each parallelogram 458 divided into two triangular panels 460. The bistable layer 440 is shown rolled into a bellows in an expanded condition in FIG. 9B, and is expandable between the expanded condition in FIG. 9B and the compressed condition of FIG. 9C. The bellows is formed by rolling and connecting the lateral edges 455 and 457. In use however, the bistable layer 440 may be maintained in a collapsed condition, as shown in FIG. 9C.

Figure 9D:
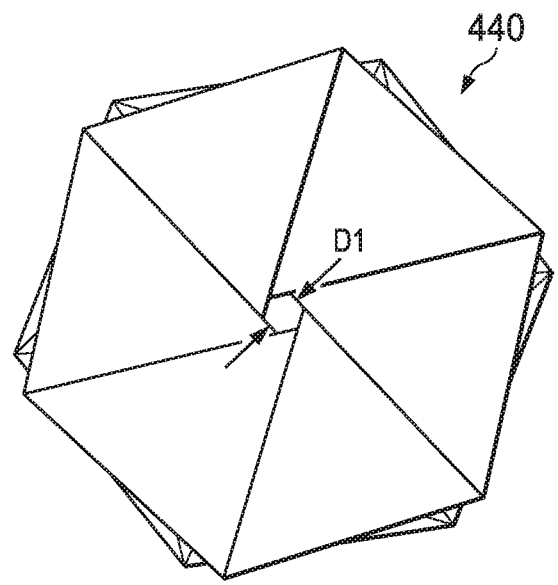
FIG. 9D is a top view diagram of an origami bellows formed of the portion of the sheet material shown in FIG. 9A according to some implementations of the present disclosure.

FIG. 9D shows an end view of the collapsed bistable layer 440. In the collapsed condition, the bistable layer 440 has an inner diameter D1. This inner diameter, defined by the valley folds of the bistable layer 440 is fixed and constant so long as the bistable layer 440 does not expand from the collapsed condition. Accordingly, in some implementations of the origami bellows 404 in FIG. 6, the bistable layer 440 may be maintained in the collapsed condition. For example, in some implementations, an adhesive may be used between overlapping folds to maintain the monostable layer in the collapsed condition. It is the inner diameter of the monostable layers that contacts and supports the catheter 310.

Figure 10:
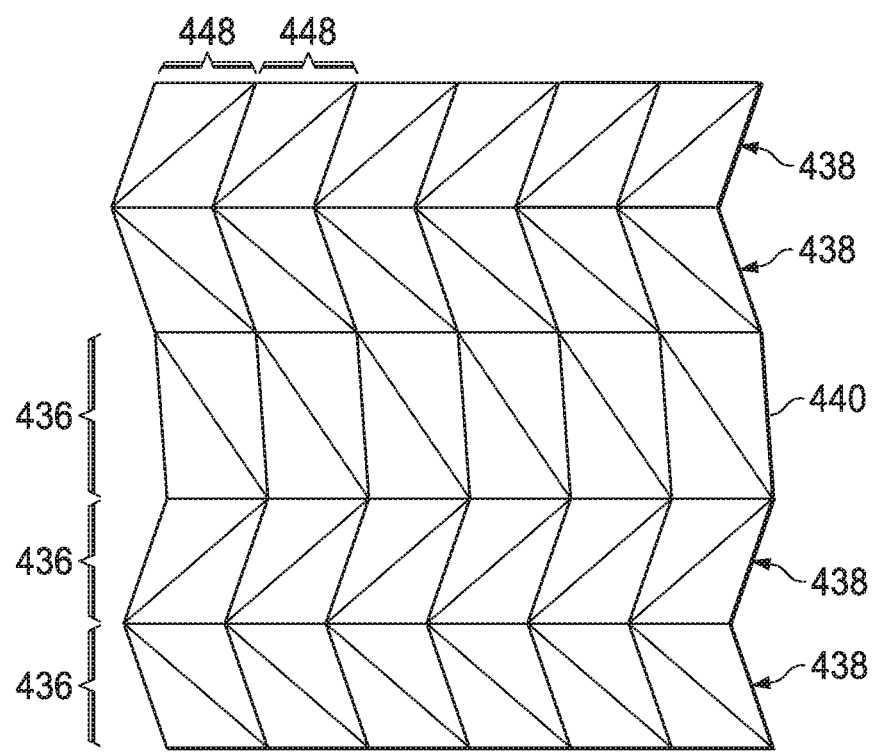
FIG. 10 is a diagram of a plan view of a sheet material for forming a portion of the origami bellows of FIG. 6 according to some implementations of the present disclosure.
Figure 11A:
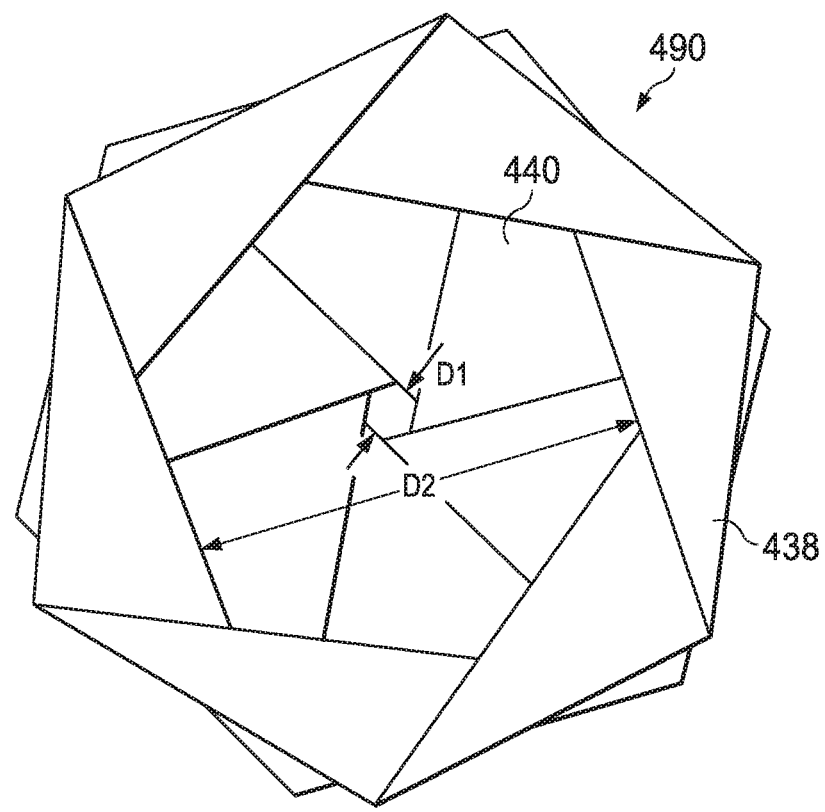
FIG. 11A is a diagram of an end view of an origami bellows formed of the portion of the sheet material shown in FIG. 10 in a deployed condition according to some implementations of the present disclosure.
Figure 11B:
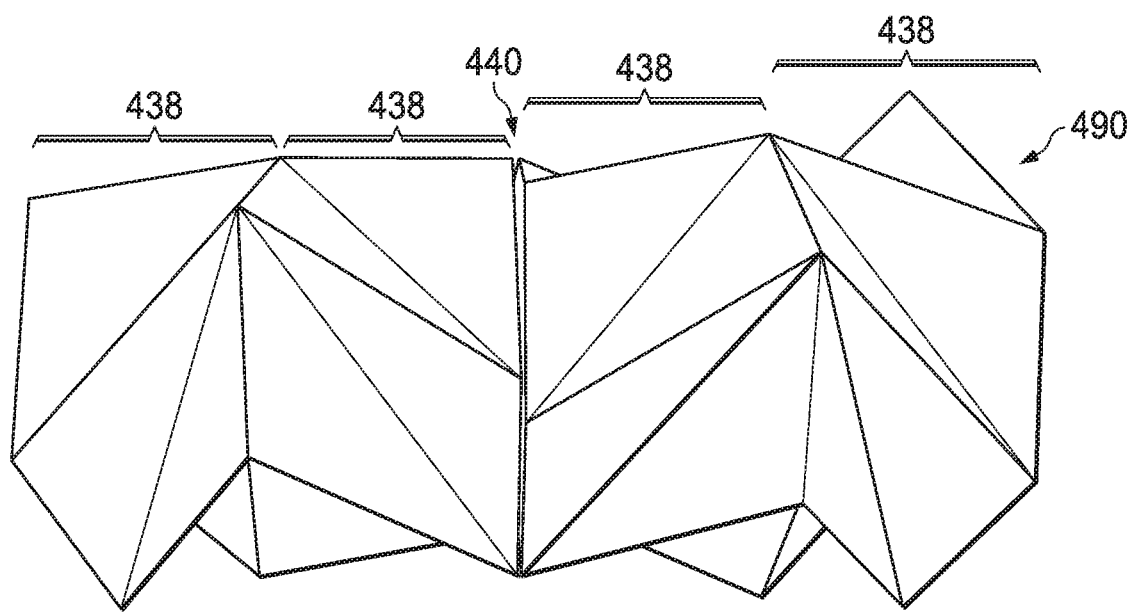
FIG. 11B is a diagram of a plan view of an origami bellows formed of the sheet material of FIG. 10 in a deployed condition according to some implementations of the present disclosure.
Figure 12A:
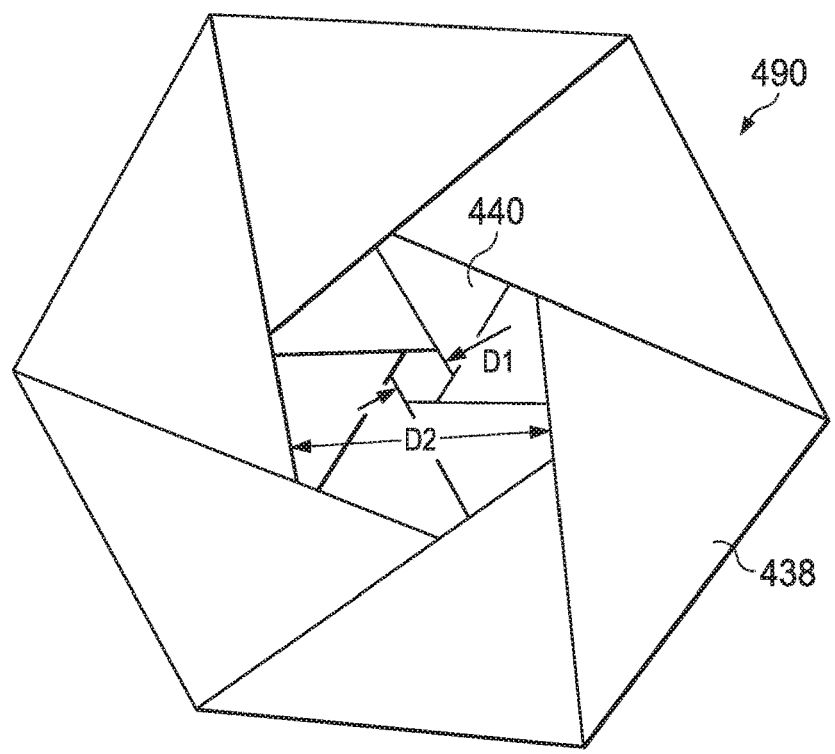
FIG. 12A is a diagram of an end view of an origami bellows formed of the portion of the sheet material shown in FIG. 10 in a collapsed condition according to some implementations of the present disclosure.
Figure 12B:
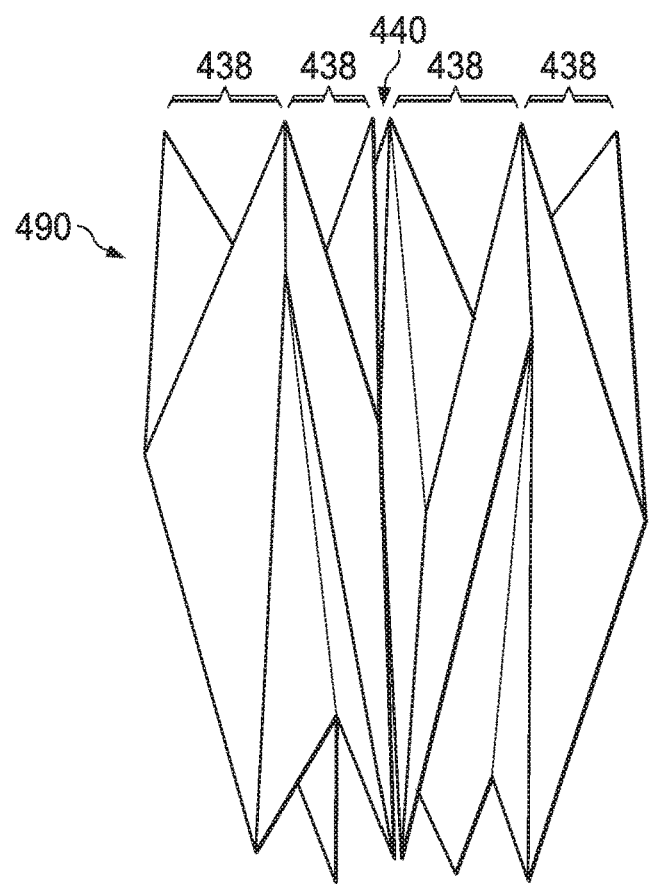
FIG. 12B is a diagram of a plan view of an origami bellows formed of the sheet material of FIG. 10 in a collapsed condition according to some implementations of the present disclosure.

The principle of expansion layers and support layers is further discussed with reference to FIGS. 10, 11A, 11B, 12A and 12B. FIG. 10 shows a sheet of five layers taken from the example of FIG. 7. In this embodiment, FIG. 10 includes two pairs of mirrored monostable layers 438, and a single bistable layer 440 disposed therebetween. FIGS. 11A and 11B show respective end and side views of an origami bellows 490 in an expanded condition formed by the sheet shown in FIG. 10. FIGS. 12A and 12B show respective end and side views of the same origami bellows 490 in a collapsed condition. FIG. 11A shows a lumen formed by inner walls of a bistable layer 440 having a diameter D1 and the monostable layer 438 having a diameter D2 when the origami bellows is in an expanded condition. FIG. 12A shows the lumen formed by inner walls of the bistable layer 440 having the same diameter D1 and the monostable layer 438 having a diameter D3 when the origami bellows 490 is in a compressed condition. In each of FIGS. 11A and 12A, the bistable layer 440 maintains the same inner diameter, while the monostable layer 438 changes its inner diameter between larger diameter D2 in the expanded condition and the smaller diameter D3 in the compressed condition.

Figure 13:
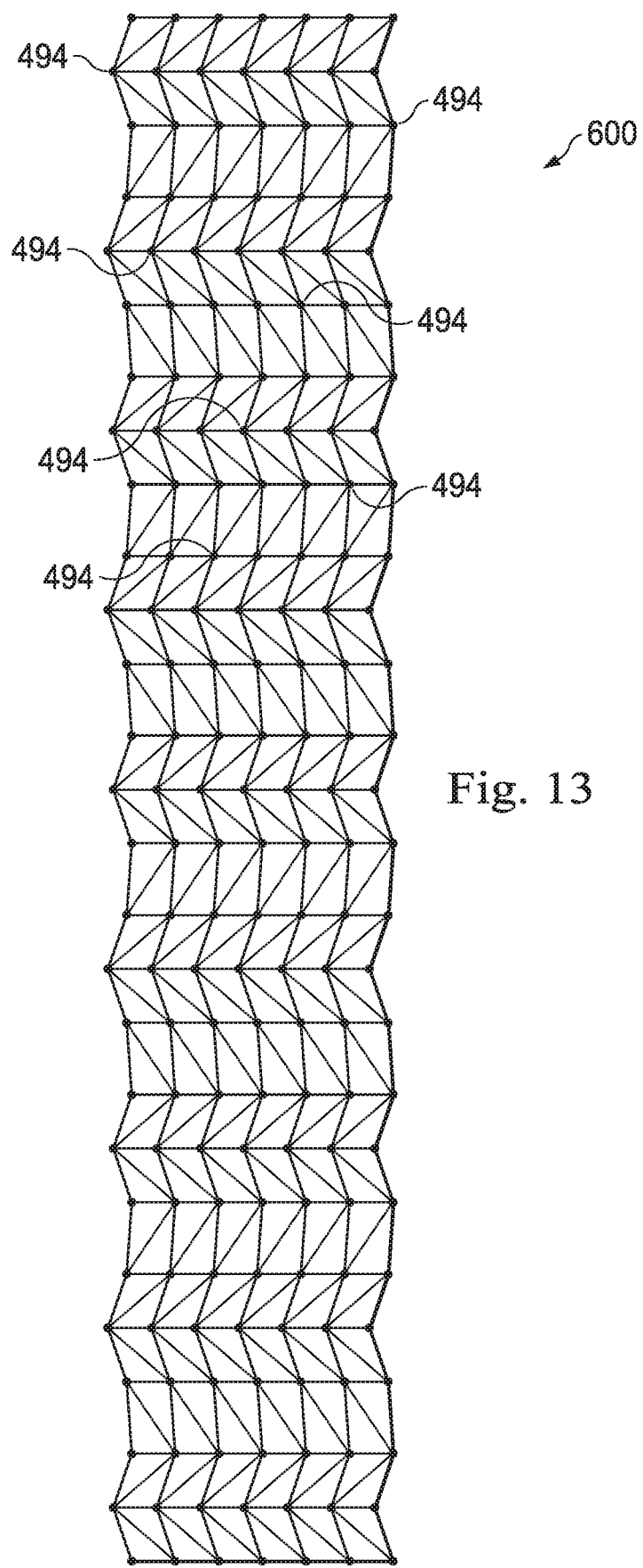
FIG. 13 is a diagram of a plan view of a sheet material for forming an origami bellows according to some implementations of the present disclosure.

FIG. 13 shows another exemplary embodiment of a foldable sheet 600 to form an origami bellows. This foldable sheet includes many of the same folds and features described in other implementations herein, and those will not be repeated here. This embodiment however includes strain relief apertures 494 at each vertex of the folds. These apertures 494 may be formed by punching or cutting holes in the sheet at the vertices. In a typical origami bellows, the vertices may be subject to the maximum strain. By including apertures 494 in the locations of the vertices, the strain applied is reduced. Because of this, the actual force required to actuate the origami bellows is also reduced. In some implementations, by reducing the strain, noise resulting from actuation may also be reduced.

Returning to FIG. 7, the distal end 428 and the proximal end 432 include a plurality of connection tabs 470. This exemplary implementation includes a connection tab 470 from each of the six parallelogram panels 448. As will be described, these connection tabs 470 may be used to secure the origami bellows 404 to the distal mount 402 and the proximal mount 406. In some implementations, these connection tabs 470 may extend into the distal mount 402 or the proximal mount 406 and may be folded or otherwise attached to the distal mount 402 or the proximal mount 406.

Figure 14:
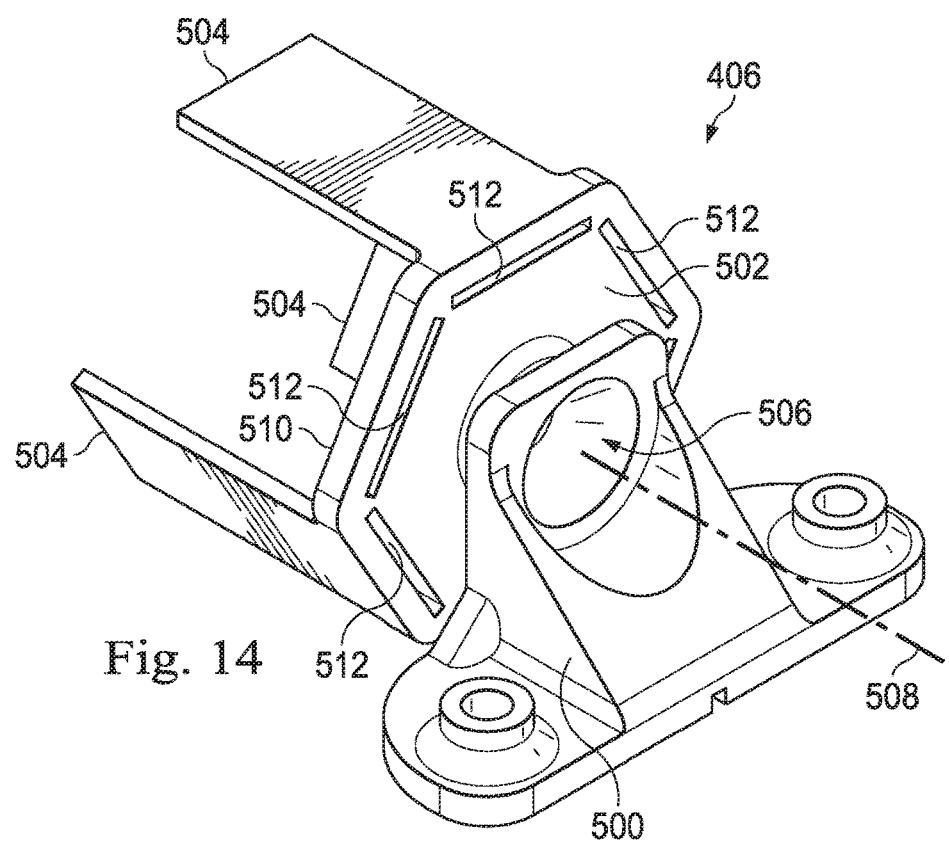
FIG. 14 is a diagram of a perspective view of a proximal mount forming a portion of the instrument guiding apparatus of FIG. 4 according to some implementations of the present disclosure.

FIG. 14 shows additional details of the proximal mount 406, which is configured to attach to the instrument interface portion 300 of FIG. 3. The proximal mount 406 includes an attachment component 500, a base element 502, and bellows-support tabs 504. A passage 506 extends through the attachment component 500 and the base element 502. The passage 506 accommodates the catheter 310, allowing the catheter to exit the end of the origami bellows. The passage 506 may define an axis 508 that may be arranged to be coaxial with the origami axis 408 of the origami bellows 404. The attachment component 500 may be configured to be attached, such as by bolts, directly to the instrument interface portion 300. The base element 502 is shown as a plate that extends over the proximal end of the origami bellows 404. In this implementation, the periphery 510 of the base element 502 is shaped to match the proximal end of the origami bellows 404. Accordingly, since the origami bellows 404 shown in FIGS. 6 and 7 includes six parallelogram panels 448, the periphery 510 of the base element 502 is shaped as a hexagon, that may match the number of parallelogram panels of the origami bellows 404. Other base element embodiments have other shapes that may match the ends of the origami bellows 404. In some implementations, the shape of the base element is not shaped to match the origami bellows 404. In addition to having the central passage 506 extending therethrough, the base element 502 includes a plurality of slots 512 that receive the connection tabs 470 disposed at the proximal end of the origami bellows 404. In the implementation shown, each slot 512 extends parallel to its adjacent peripheral edge forming the periphery of the base element 502. Again, in this implementation, since each parallelogram panel 448 includes a connection tab 470, and since there are six parallelogram panels 448 in the exemplary embodiment in FIGS. 6 and 7, the base element 502 includes six slots to receive the six connection tabs 470. Other implementations may have a different number of parallelogram panels per layer, and likewise, other implementations may have a different number of connection tabs 470 irrespective of the number of parallelograms per layer. Likewise, other implementations of the base element 502 may have a different number of slots for receiving the connection tabs 470. In use, a connection tab 470 may extend through one of the slots 512, and may be glued, welded, taped, deformed, or otherwise attached to the base element 502. In some implementations, the origami bellows is attached to the proximal mount 406 in other ways. For example, some embodiments include connection tabs on the base element 502, and the proximal end of the origami bellows is configured to receive and attach to the connection tabs from the base element 502. In other implementations, the origami bellows connects to the bellows-support tabs 504 on the proximal mount 406. Yet other connection mechanisms are contemplated.

The bellows-support tabs 504 on the proximal mount 406 extend from the periphery 510 of the base element 502 in the distal direction. The bellows-support tabs 504 are spaced apart from each other a sufficient distance to extend along the outer surface of the origami bellows 404. The bellows-support tabs 504 may provide stability to the origami bellows 404 helping constrain deflection due to gravity, helping maintain the origami bellows 404 between the distal and proximal mount 402, 406. The exemplary proximal mount shown includes three bellows-support tabs offset from one another. As would be apparent to one of ordinary skill in the art, any number of bellows-support tabs may be included on the proximal mount 406. Some implementations do not include bellows-support tabs.

Figure 15:
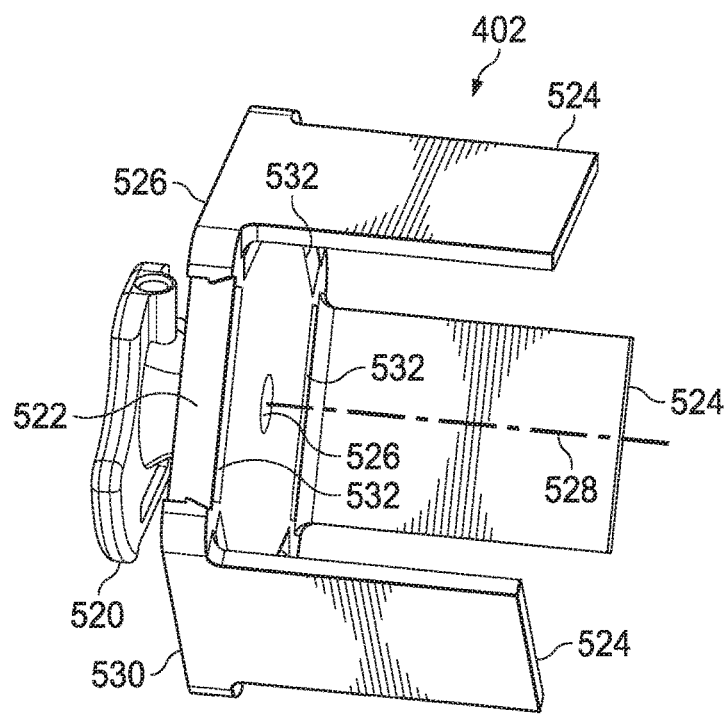
FIG. 15 is a diagram of a perspective view of a distal mount forming a portion of the instrument guiding apparatus of FIG. 4 according to some implementations of the present disclosure.

FIG. 15 shows additional detail of the distal mount 402. The distal mount 402 includes an attachment element 520, a base element 522, and bellows-support tabs 524. A passage 526 extends through the attachment element 520 and the base element 522. The passage 526 is sized and configured to permit the catheter 310 to pass through the distal mount (and likewise extend out of an origami bellows 404 attached to the distal mount) toward the patient. The attachment element 520 is shaped and configured to attach to the instrument interface portion 300 of FIG. 3. Therefore, it serves as a stabilizing element to secure the distal mount in a position that aligns the catheter passing therethrough with an introducer or other components configured to introduce the catheter to the patient. The base element 522 is similar to the base element 502 of the proximal mount 406 described above. As such, it is configured to interface with the distal end of the origami bellows 404. The base element 522 has a periphery 530 and includes a plurality of slots 532 configured to receive connection tabs on the distal end of the origami bellows 404 in the manner described above with reference to the proximal mount 406. The bellows-support tabs 524 project from the distal mount 402 and the proximal direction and are spaced and aligned to receive the distal end of the origami bellows. In the implementation shown 1n FIGS. 14-15, both the distal mount 402 and the proximal mount 406 include three bellows-support tabs. The bellows-support tabs 504 may be radially offset from the bellows-support tabs 524, so as to not interfere with each other when in an overlapping condition. As described above, the distal mount may include any number of bellows-support tabs 524 or may be devoid of bellows-support tabs 524.

Referring back to FIG. 4 showing the instrument guiding apparatus 302, the proximal mount 406 is configured to attach to the distal mount 402. This may maintain the origami bellows in a compressed and convenient package for transport and assembly onto the instrument interface portion 300. In this implementation, the bellows-support tabs 504 include connection mechanisms 540 (also shown in FIG. 5), shown herein as the deflective arrowheads, that engage the base element 522 of the distal mount 402. In this implementation, the base element 522 includes a connection mechanism 542 configured to interface with the connection mechanism 540. In this implementation using deflective arrowheads, the connection mechanism 542 may comprise a shoulder configured to receive a backside of the arrowhead. In this manner, the proximal mount 406 may be attachable to the distal mount 402 to maintain the origami bellows 404 in a convenient package. As can be seen in this implementation, the bellows-support tabs 524 of the distal mount 402 have a length less than the length of the bellows-support tabs 504 of the proximal mount 406. However, the bellows-support tabs may have any desired length. In this implementation, the bellows-support tabs 504, 524 are radially offset so as to not interfere with each other when the origami bellows is in the compressed condition.

In use, the instrument guiding apparatus 302 may be introduced to the instrument interface portion 300 in a compressed condition. A catheter may be introduced through the passage in either the distal or proximal mount, through the origami bellows 404, and through the passage in the other of the distal and proximal mount. The origami bellows 404 may provide lateral support to the catheter at each of the supporting layers in the bellows. The proximal and distal mounts may be unattached from each other and translated relative to each other to expand the origami bellows, and prepare the catheter for insertion to a patient. This may expand the origami bellows from the collapsed condition to an expanded condition. In such an expansion, the actuating layers may separate or expand, while the support layers may not. As such, the support layers may maintain their same inner diameter, and may continue to provide support to the catheter. Obviously, adjacent support layers would now be spaced further apart than when the origami bellows is in the collapsed condition. Accordingly, instead of providing continuous lateral support to the catheter, the spaced apart support layers of the origami bellows may provide spaced support along the length of the origami bellows. In preparation for or during a surgical procedure, the proximal mount 406 may axially displace toward the distal mount, advancing the catheter through the distal mount toward the patient. As this occurs, the origami bellows may advance from its expanded condition toward its collapsed condition. Through this, the actuation layers, formed of monostable elements, may begin to compress. The support layers, formed of bistable layers, may generally maintain their same condition, resulting in little or no change in the inner diameter of the support layers. As the flexible catheter advances toward the patient, it may be inclined to bend or resist advancement. However, the support layers may prevent or reduce the likelihood of buckling by constraining the catheter as the catheter advances toward the patient. In this manner, the support layers provide radial support to the catheter.

In the examples of implementations described herein, bistable actuating layers are combined in an alternating matter with monostable layers. To prevent rotation of the proximal and distal ends of the origami bellows, the monostable layers are provided in pairs of mirrored layers. In addition, an even number of stable or support layers are also provided and arranged to offset rotation that may occur. In an exemplary implementation, the origami bellows has eighteen monostable layers with eight bistable layers, with each bistable layer disposed in between a monostable layer pair. The bistable layers create the small inner diameter section that acts as a radial anti-buckling support. However, it is worth noting that the number and height of layers can be manipulated to tailor the performance and the total extended length. Because the number of monostable layers was kept even in order to cancel individual layer rotation, the overall rotation of the origami bellows may remain at 0 during operation. The crease or fold pattern in some implementations may be scored into the sheet using a laser cutter.

In some implementations, the holes at the vertices may be formed by laser cutting. As described above tension may be induced in the origami bellows to mitigate buckling, but as the origami bellows approaches the compressed condition, and as tension decreases, the bellows-support tabs of the distal and proximal mounts may provide lateral support. In some embodiments, the bellows-support tabs may have a length between 20 mm and 80 mm, although larger and smaller lengths are contemplated. Compliant locking members can be built into the tabs to keep the pattern locked into a stowed state. The sheet material forming the origami bellows may be formed of any flexible, foldable material. In some examples, the origami bellows is formed of a polymer film, organic materials such as a paper product, composite materials metal or foil materials, among others. In one example, the origami tube is formed of a Polyethylene Terephthalate (PET) film. In some implementations, the origami bellows may be sterilizable, and may be resistant to temperatures. In some implementations, the origami bellows is a single use material that may be disposed of after each surgical application. In other implementations, the origami bellows may be reused.

Although described to provide lateral support and as an anti-buckling guide for a catheter system, the origami bellows described herein may find application in other areas. For example, the system may be used anywhere a variable orifice is needed. This may include pumps or throttle systems which can be made from a single material. In some implementations, the origami bellows can be made to completely close the bellows with a bistable layer having an inner diameter of 0. As such, this may create a built-in cap for pipes or tubes.

While certain exemplary implementations of the invention have been described and shown in the accompanying drawings, it is to be understood that such implementations are merely illustrative of and not restrictive on the broad invention, and that the implementations of the invention not be limited to the specific constructions and arrangements shown and described, since various other modifications may occur to those ordinarily skilled in the art.

What is claimed is:

1. An apparatus for laterally supporting a flexible elongate device introducible using a manipulator assembly, the apparatus comprising:
an origami bellows having a distal end, a proximal end, and a lumen extending from the distal end to the proximal end, the origami bellows having a fixed diameter portion configured to support the flexible elongate device and having a non-fixed diameter portion that changes when the origami bellows is axially compressed from an expanded condition to a compressed condition;
a first connector disposed at and coupled to the distal end, the first connector being configured to connect the distal end to the manipulator assembly; and
a second connector disposed at and coupled to the proximal end, the second connector being configured to connect the proximal end to the manipulator assembly.

2. The apparatus of claim 1, wherein the lumen is sized to provide lateral support to the flexible elongate device when, during compression and expansion of the origami bellows, the flexible elongate device extends therethrough.

3. The apparatus of claim 1, wherein the first connector or the second connector comprises a passage formed therein aligned with a longitudinal axis of the lumen of the origami bellows, the passage being sized to permit passage of the flexible elongate device into the lumen of the origami bellows.

4. The apparatus of claim 1, wherein the origami bellows comprises a plurality of mirrored pairs of layers formed by folds, the pairs of layers having offsetting rotational directions to prevent rotation of the distal end and the proximal end.

5. The apparatus of claim 1, wherein the origami bellows has an inner diameter in a range of 3 mm to 7 mm to accommodate the flexible elongate device when the origami bellows is in the compressed condition.

6. The apparatus of claim 1, wherein the origami bellows and the first and the second connectors are single use materials.

7. The apparatus of claim 1, wherein the origami bellows and the first connector and the second connector are sterilizable.

8. The apparatus of claim 1, wherein the origami bellows is formed from a single, monolithic sheet of material.

9. A method comprising:
introducing a flexible elongated instrument into a lumen of an origami bellows, the lumen having walls forming an inner diameter configured to support the flexible elongate device and having walls forming an inner diameter that changes when the origami bellows is axially actuated; and
advancing the flexible elongated instrument while simultaneously compressing the origami bellows so that walls of the lumen laterally support the flexible elongated instrument and reduce a likelihood of buckling of the flexible elongated instrument.

10. The method of claim 9, wherein the inner diameter of the lumen maintains a substantially constant size during compression of the origami bellows.

11. The method of claim 9, further comprising introducing the flexible elongated instrument into a passage of a first connector aligned with the lumen of the origami bellows so that the flexible elongated instrument extends through the passage and into the lumen.

12. The method of claim 9, further comprising introducing the flexible elongated instrument into a first passage of a first connector supporting a distal end of the origami bellows and into a second passage of a second connector supporting a proximal end of the origami bellows.

13. The method of claim 9, wherein the origami bellows comprises a plurality of mirrored pairs of layers formed by folds, and wherein the mirrored pairs offsetting rotation of the origami bellows when compressing the origami bellows.

14. The method of claim 9, wherein the origami bellows is formed from a single, monolithic sheet of material.

15. A deployable origami bellows apparatus configured to laterally support a flexible elongate device for patient treatment, comprising:
a distal end;
a proximal end;
a lumen extending from the distal end to the proximal end, the origami bellows being configured to axially actuate between an expanded condition to a compressed condition; and
a plurality of layers including:
at least one monostable layer, the monostable layer being stable in one of a compressed or extended condition, and
at least one bistable layer adjacent the monostable layer, the bistable layer being stable in the compressed condition and in the expanded condition.

16. The apparatus of claim 15, wherein the at least one bistable layer comprises a substantially constant inner diameter in the compressed condition and in the expanded condition.

17. The apparatus of claim 15, comprising apertures formed at locations of fold vertices in the at least one monostable layer or the at least one bistable layer.

18. The apparatus of claim 15, comprising at least two monostable layers and at least two bistable layers, the monostable layers being combined with the bistable layers in alternating order, and wherein the at least one monostable layer is stable in the expanded condition.

19. The apparatus of claim 15, comprising one of:
an even number of mono stable layers to inhibit rotation of the origami bellows; or
an even number of bistable layers that inhibits rotation.

20. The apparatus of claim 15, comprising axially extending connection tabs extending from the distal end or the proximal end of the origami bellows.